United States Patent
Kang et al.

(10) Patent No.: US 9,290,739 B2
(45) Date of Patent: Mar. 22, 2016

(54) EQUINE AMNIOTIC FLUID-DERIVED MULTIPOTENT STEM CELLS AND A METHOD FOR PRODUCING THE SAME

(75) Inventors: Kyung Sun Kang, Seoul (KR); Min Soo Seo, Daegu (KR); Sang Bum Park, Seoul (KR)

(73) Assignee: KANG STEM BIOTECH CO., LTD., Seoul (KR)

( * ) Notice: Subject to any disclaimer, the term of this patent is extended or adjusted under 35 U.S.C. 154(b) by 32 days.

(21) Appl. No.: 13/821,303

(22) PCT Filed: Sep. 7, 2011

(86) PCT No.: PCT/KR2011/006637
§ 371 (c)(1),
(2), (4) Date: Apr. 24, 2013

(87) PCT Pub. No.: WO2012/033352
PCT Pub. Date: Mar. 15, 2012

(65) Prior Publication Data
US 2013/0230924 A1    Sep. 5, 2013

(30) Foreign Application Priority Data
Sep. 8, 2010  (KR) ........................ 10-2010-0088144

(51) Int. Cl.
C12N 5/07       (2010.01)
C12N 5/071      (2010.01)
C12N 5/077      (2010.01)
A61K 35/50      (2015.01)
C12N 5/073      (2010.01)
C12N 5/0775     (2010.01)
C12N 5/0735     (2010.01)

(52) U.S. Cl.
CPC .............. *C12N 5/0655* (2013.01); *A61K 35/50* (2013.01); *C12N 5/0605* (2013.01); *C12N 5/0606* (2013.01); *C12N 5/0653* (2013.01); *C12N 5/0654* (2013.01); *C12N 5/0668* (2013.01)

(58) Field of Classification Search
CPC ..... C12N 5/0605; C12N 5/0607; A61K 35/50
USPC .................. 435/377, 395, 378, 325
See application file for complete search history.

(56) References Cited

FOREIGN PATENT DOCUMENTS

KR     100950195 B1    3/2010
WO     2008036374 A2   3/2008

OTHER PUBLICATIONS

In 't Anker et al., Amniotic fluid as a novel source of mesenchymal stem cells for therapeutic transplantation. Blood, vol. 102, No. 4 (2003) pp. 1548-1549.*
Cananzi et al., Stem cells derived from amniotic fluid; new potentials in regenerative medicine. Bioscience and Life, vol. 4 No. 1 (Mar. 2009) pp. 17-27.*
Noort et al., Mesenchymal stem cells promote engraftment of human umbilical cord blood-derived CD34+ cells in NOD/SCID mice. Experimental Hematology, vol. 30 (2002) pp. 870-878.*
Zheng et al., Characterization and hepatogenic differentiation of mesenchymal stem cells from human amniotic fluid and human bone marrow: A comparative study. Cell Biology International, vol. 32, No. 11 (Nov. 2008) pp. 1439-1448.*
Amniomax II. Datasheet [online]. Life Technologies, 2015 [retrieved on Mar. 26, 2014]. Retrieved from the Internet: <URL: https://www.lifetechnologies.com/order/catalog/product/11269016>.*
Labitzke, R., & Freidl, P., A serum-free medium formulation supporting growth of human umbilical cord vein endothelial cells in long-term cultivation. Cytotechnology, vol. 35 (2001) pp. 87-92.*
Freshney, R. Ian, Defined Media and Supplements (Chapter 8) in Culture of Animal Cells: A Manual of Basic Technique and Specialized Applications, Sixth Edition. (John Wiley & Sons Hoboken, NJ, online Mar. 9, 2011) pp. 99-114. QH585.2.F74 2010.*
Colter, David C., et al., "Rapid expansion of recycling stem cells in cultures of plastic-adherent cells from human marrow," PNAS (2000) 97:7 pp. 3213-3218.
De Mattos Carvalho, Armando et al., "Isolation and immunophentypic characterization of mesenchymal stem cells derived from equine species adipose tissue," Veterinary Immunology and Immunopathology (2009) 132 pp. 303-306.
Dominici, M., et al., "Minimal criteria for defining multipotent mesenchymal stromal cells. The International Society for Cellular Therapy position statement," Cytotherapy (2006) 8:4 pp. 315-317.
Koch, Thomas G., et al., "Isolation of mesenchymal stem from equine umbilical cord blood," BMC Biotechnology (2007) 7:26 pp. 1-9.
Masson, Neil M., et al., "Hepatic progenitor cells in human fetal liver express the oval cell marker Thy-1," Am J Physiol Gastroinest Liver Physiol (2006) 291 pp. G45-G54.
Park, Sang-Bum, et al., "Isolation and characterization of equine amniotic fluid-derived multipotent stem cells," Cytotherapy (2011) 13 pp. 341-349.
Reya, Tannishtha, et al., "Stem cells, cancer, and cancer stem cells," Nature (2001) 414 pp. 105-111.
Tsai, Ming-Song, et al., "Isolation of human multipotent mesenchymal stem cells from second-trimester amniotic fluid using a novel two-stage culture protocol," (2004) Human Reproduction 19:6 pp. 1450-1456.
Duarte, Sergio et al., "Human serum as an alternative for amniotic fluid stem cells culture media for clinical us," FASEB J. (2009) (Meeting Abstract Supplement), 1030.1, URL: http://fasebj.org/cgi/conent/meeting_abstract/23/1_MeetingAbstracts/1030.1.

(Continued)

*Primary Examiner* — Laura Schuberg
*Assistant Examiner* — Kara Johnson
(74) *Attorney, Agent, or Firm* — Edwin S. Flores; Chainey P. Singleton; Chalker Flores, LLP (57) ABSTRACT

The present invention relates to equine amniotic fluid-derived multipotent stem cells (Eaf-MSCs) and a preparation method thereof. More particularly, the present invention relates to equine amniotic fluid-derived multipotent stem cells which exhibit all negative immunological characteristics with respect to the human markers, CD19, CD20, CD28, CD31, CD34, CD38, CD41A, CD62L, CD62P and CD200, and exhibit all positive immunological characteristics with respect to the human markers, CD44, CD90 and CD105, and have the ability to differentiate into ectoderm, mesoderm or endoderm-derived cells.

8 Claims, 5 Drawing Sheets

(56) References Cited

OTHER PUBLICATIONS

Heydarkhan-Hagvall, Sepideh et al., "Human Adipose Stem Cells: A Potential Cell Source for Cardiovascular Tissue Engineering," Cells Tissues Organs (Jan. 14, 2008) vol. 187, pp. 263-274.

Kim, Gi Dae et al., "Differentiation of endothelial cells derived from mouse embryoid bodies: A possible in vitro vasculogenesis model," Taxicology Letters (2006) Vo., 180, pp. 166-173.

Sariboyyaci, A. Eker et al., "Isolation, Characterization and Differentation Potential of Human Amniotic Fluid Derived Multipotent Mesenchymal Stem Cells," Haematoiogica (2009) 94(s2): 458-459.

European Extended Search Report [EP11823785.8] dated Feb. 2014.

Carrade, Danielle D. et al., "Clinicopathologic findings following intra-articular injection of autologous and allogenic placentally dervied equine mesenchymal stem cells in horses," Cytotherapy, 2011; 13: 419-430.

Guest, Deborah J. et al., "Defining the expression of marker genes in equine mesenchymal stromal cells," Stem Cells and Cloning: Advances and Applications, 2008; 1: 1-9.

Hoynowski, Steven M. et al., "Characterization and differentiation of equine umbilical cord-derived matrix cells," Biochemical and Biophysical Research Communications, 2007; 362: 347-353.

Iacono, E. et al., "384 Isolation of Mesenchymal Stem Cells from Wartons Jelly, Cord Blood, and Amniotic Fluid in the Horse," Reproduction, Fertility and Development, 2009; 22: 348-349.

Iacono, E. et al., "Isolation, characterization and differentiation of mesenchymal stem cells from amniotic fluid, umbilical cord blood and Wharton's jelly in the horse," Reproduction Research, 2012; 143: 455-468.

Koch, Thomas G. et al., "Current and future regenerative medicine—Principles, concepts, and therapeutic of stem cell therapy and tissue engineering in equine medicine," CVJ, Feb. 2009; 50: 155-165.

Lovati, Arianna Barbara et al., "Comparision of equine bone marrow-, umbilical cord matrix and amniotic fluid-derived progenitor cells," Vet Res Commun, 2011; 35: 103-121.

Perin, Laura et al., "Characterization of Huiman Amniotic Fluid Stem Cells and Their Pluripotential Capability," Methods in Cell Biology, 2008; 86: 85-99.

Mizuno, Hiroshi et al., "Mesengenic Potential and Future Clinical Perspective of Human Processed Lipoaspirate Cells," J Nippon Med Sch, 2003; 70/4: 300-306.

Muttini, A. et al., "Experimental study on allografts of amniotic ewpithelial cells in calcaneal tendon leasions of sheep," Vet Res Commun, 2010; 34-(Supp 1): S117-S120.

Pascucci, L. et al., "Flow cytometric characterization of culture expanded multipotent mesenchymal stromal cells (MSCs) from horse adipose tissue: Towards the definition of minimal stemness criteria," Veterinary Imminology and Immunopathology, 2011; 144: 499-506.

Richarson, Lucy E., "Stem cells in veterinary medicine—attempts at regenerating equine tendon after injury," Trends in Biotechnology, 2007; 25/9: 409-416.

Zhang, Ping et al., "Endothelial Differentiation of Amniotic Fluid-Derived Stem Cells: Synergism of Biochemical and Shear Force Stimuli," 2009; 18/9: 1299-1308.

* cited by examiner

EQUINE AMNIOTIC FLUID-DERIVED MULTIPOTENT STEM CELLS AND A METHOD FOR PRODUCING THE SAME

BACKGROUND OF THE INVENTION

1. Field of the Invention

The present invention relates to equine amniotic fluid-derived multipotent stem cells (eAF-MSCs) and a preparation method thereof. More specifically, the present invention relates to equine amniotic fluid-derived multipotent stem cells which exhibit all negative immunological characteristics with respect to the human markers CD19, CD20, CD28, CD31, CD34, CD38, CD41a, CD62L, CD62P and CD200, and exhibit all positive immunological characteristics with respect to the human markers CD44, CD90 and CD105, and have the ability to differentiate into ectoderm, mesoderm or endoderm-derived cells and the ability to maintain an undifferentiated state for 14 passages or more.

2. Description of the Related Art

Biotechnology in the $21^{st}$ century presents the possibility of new solutions to food, environmental and health problems, with the ultimate object of promoting human prosperity. In recent years, the technology of using stem cells has been considered as a new way to treat incurable diseases. Previously, organ transplantation, gene therapy, etc., were considered for the treatment of incurable diseases. However, their efficient use has not been achieved due to factors such as rejection by the immune system, the short supply of organs, and an insufficient knowledge of disease genes For these reasons, there has been an increased interest in the study of stem cells and it has been recognized that totipotent stem cells, having the ability to form all the organs by proliferation and differentiation, can not only treat most diseases but can also fundamentally heal organ injuries. Also, many scientists have suggested clinical applicability of stem cells for the regeneration of all the organs and the treatment of incurable diseases, including Parkinson's disease, various cancers, diabetes and spinal damages.

Stem cells refer to cells having not only self-replicating ability but also the ability to differentiate into at least two cells, and can be divided into totipotent stem cells, pluripotent stem cells, and multipotent stem cells (MSCs).

Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called embryonic stem cells and can differentiate into various other tissue cells but not form new living organisms.

Multipotent stem cells were first isolated from adult bone marrow (Y. Jiang et al., Nature, 418:41, 2002), and then also found in other various adult tissues (C. M. Verfaillie, Trends Cell Biol., 12:502, 2002). In other words, although bone marrow is the most widely known source of stem cells, the multipotent stem cells were also found in the skin, blood vessels, muscles and brains (J. G. Toma et al., Nat. Cell Biol., 3:778, 2001; M. Sampaolesi et al., Science, 301:487, 2003; Y. Jiang et al., Exp. Hematol., 30:896, 2002). However, stem cells are very rarely present in adult tissues, such as bone marrow, and such cells are difficult to culture without inducing differentiation, and thus difficult to culture in the absence of specifically screened media.

Equine is a mammal belonging to the Equidae (Genus *Equus*), and very familiar with humans, along with dogs or cats. Equine industries, including the horse racing industry, are growing worldwide. In the horse racing industry, because the value depends on the horse's pedigree, injuries of racehorses with a good pedigree are a major problem. Thus, the development of cell therapy has attracted attention. Considering the size of racehorses, it was a main technical issue to reliably supply a large number of cells.

Therefore, isolation and characterization of stem cells derived from various equine tissues are important issues in the stem cell field. Conventionally, there have been many attempts to isolate stem cells from human and mouse tissues. However, cell therapy for the treatment of muscle, bone, cartilage, tendon or muscle of horses, in particular racehorses, has not yet been actively studied.

There is a report on the isolation of stem cells from equine adipose tissues (Armando de Mattos Carvalho et al., Veterinary Immunology and Immunopathology, 132:303, 2009), but, unlike other mammals, horses do not have much adipose tissue, and thus there is a difficulty in obtaining them. In addition, stem cell isolation from adipose tissue is a painful invasive procedure. Isolation of stem cells from equine bone marrow is also an invasive procedure, as in the procedure of the adipose tissue. Due to the nature of racehorses, there is also a limitation in the isolation of stem cells from adipose tissue or bone marrow.

At the present technical level, to use adult stem cells as the cell therapeutic agent, it is required to standardize the culture conditions under which the undifferentiated state can be maintained. In addition, since adult stem cells isolated from tissues are present in the mixed state of various kinds of cells, technology is sought that is capable of culturing homogeneous adult stem cells on a mass scale. In particular, the method for isolating adult stem cells from tissues or blood generally includes, for example, cell sorting utilizing antibodies for numerous surface antigens. However, this method has the limitation that the surface antigens for adult stem cells should be understood, and further, its use is greatly restricted by the problems that the common surface antigen (hereinafter, referred to as "marker") for adult stem cells is not known. Also, markers for adult stem cells are not variously developed, and further, even the known markers show different degrees of expression depending on the differentiation state. Additionally, the sorting equipment is expensive.

Further, adult stem cells may possibly be mixed with other mononuclear cells and other stem cells in amniotic fluid. However, such mixed cell culture conditions may result in a difference in the distribution degree of nutrients, thereby leading to the heterogeneity of cell differentiation state. In the end, the problem that the cells cannot be produced as the homogeneous cell population serves as the fatal disadvantage that when they are used as the therapeutic agent, the actual effect may be different from the intended effect. Therefore, there is an urgent need for development of the effective culture technology which can provide homogeneous adult stem cells in a large quantity.

Accordingly, the present inventors first isolated stem cell populations with improved homogeneity from equine amniotic fluid as a new source of cell supply. They found that these cells exhibit more rapid and steady self-renewal ability (growth ability) than other stem cells, immunological characteristics of multipotent stem cells, and excellent multilineage differentiation capability, in particular, outstanding osteogenic differentiation capability, thereby completing the present invention.

SUMMARY OF THE INVENTION

An object of the present invention is to provide multipotent stem cells as equine amniotic fluid-derived adult stem cells.

Another object of the present invention is to provide a method for preparing the equine amniotic fluid-derived multipotent stem cells.

Still another object of the present invention is to provide a method for differentiating the equine amniotic fluid-derived multipotent stem cells into various types of cells.

Still another object of the present invention is to provide a cell therapeutic agent comprising the equine amniotic fluid-derived multipotent stem cells or cells differentiated therefrom as an active ingredient.

DETAILED DESCRIPTION OF THE PREFERRED EMBODIMENTS

In order to achieve the above objects, the present invention provides equine amniotic fluid-derived multipotent stem cells which exhibit all negative immunological characteristics with respect to the human markers CD19, CD20, CD28, CD31, CD34, CD38, CD41a, CD62L, CD62P and CD200, and exhibit all positive immunological characteristics with respect to the human markers CD44, CD90 and CD105, and have the ability to differentiate into ectoderm, mesoderm or endoderm-derived cells and the ability to maintain an undifferentiated state for 14 passages or more In the present invention, the equine amniotic fluid-derived multipotent stem cells can be characterized by having the ability to differentiate into chondrocytes, osteocytes or adipocytes.

Further, the present invention provides a method for preparing equine amniotic fluid-derived multipotent stem cells showing the above characteristics and being more homogeneous than those before culture, comprising Step 1 of culturing stem cells isolated from equine amniotic fluid in EGM™-2 (Endothelial Cell Growth Medium-2); and Step 2 of recovering the cultured cells.

Further, the present invention provides a cell therapeutic agent comprising equine amniotic fluid-derived multipotent stem cells or chondrocytes, osteocytes, adipocytes, tenocytes or myocytes that are differentiated from the stem cells, as an active ingredient.

Amniotic fluid refers to a liquid that is contained in the amniotic sac, and plays a role in the protection of the fetus. Amniotic fluid acts as a buffer against external stimulation and as a barrier against bacterial infections.

Stem cells refer to cells having not only self-replicating ability but also the ability to differentiate into at least two cells, and adult stem cells refer to stem cells that are present during embryonic development or in the adult body.

Equine refers to an animal belonging to the Genus *Equus*, and includes Subgenus *Hippotigris*, Subgenus *Equus*, Subgenus *Asinus*, and Subgenus *Hippotigris+Asinus*.

Unless defined otherwise, all technical and scientific terms used herein have the same meaning as commonly understood by one of ordinary skill in the art, to which this invention belongs. Generally, the nomenclature used herein and the laboratory procedures described below are those well known and commonly employed in the art.

Hereinafter, the present invention will be described in detail.

MSCs are generally incubated as the heterogeneous population. During the proliferation, the cell population is diversified in view of the self-renewal and plasticity. Therefore, it is required to isolate a more homogenous cell population.

There is a report that the conventional multipotent stem cells isolated from equine adipocytes exhibit negative immunological characteristics with respect to the human marker CD13 (4.27%) and all positive immunological characteristics with respect to the human marker CD44 (73.68%) and the human markers CD44 and CD90 (92.14%) (Armando de Mattos Carvalho et al., Veterinary Immunology and Immunopathology, 132:303, 2009).

However, in the present invention, stem cells isolated from equine amniotic fluid were cultured in EGM™-2 and subsequently in DMEM. Flow cytometry analysis of the cultured cells was performed using antibodies against specific human markers. They showed low levels (2.81% or lower) with respect to the human markers CD19, CD20, CD28, CD31, CD34, CD38, CD41a, CD62L, CD62P and CD200, and high levels (95.10% or higher) with respect to the CD44, CD90 and CD105. Thus, a method capable of isolating more homogeneous stem cell populations than the conventional method could be established. At this time, the antibodies are those showing cross-reactivity among different species.

The present invention is characterized in that the phenotype of equine amniotic fluid-derived MSCs can be distinguished from various types of cells present in equine amniotic fluid using antibodies against the human markers CD19, CD20, CD28, CD31, CD34, CD38, CD41a, CD62L, CD62P, CD200, CD44, CD90, CD105, in the absence of various equine-specific antibodies used in flow cytometry.

Further, the present invention confirmed that stem cell populations showing all negative immunological characteristics with respect to the human markers CD19, CD20, CD28, CD31, CD34, CD38, CD41a, CD62L, CD62P and CD200, and showing all positive immunological characteristics with respect to the human markers CD44, CD90 and CD105 exist in equine amniotic fluid. The present invention is characterized in that specific stem cell populations can be isolated from equine amniotic fluid by the immunological characterization, and these stem cell populations have the ability to differentiate into ectoderm, mesoderm or endoderm-derived cells and the ability to maintain an undifferentiated state for 14 passages or more.

Herein, the human marker CD44 is a cell-surface glycoprotein and has a role in migration of MSC. The human marker CD90 is also called Thy-1 and is a marker for various kinds of stem cells (keratinocyte stem cells, endometrial stem cells and mesenchymal stromal cells) (Masson N M. et al., Am. J. Phsiol. Gastrointest Liver Physiol., July; 290(1):G45-54, 2006). The human marker CD105 is also called endoglin and is a well-known MSC marker (Dominici M. et al.).

Meanwhile, other equine markers for immune cells (CD19, CD20, CD28, CD38, CD62L and CD200), endothelial cells (CD31 and CD62P), hematopoietic cells (CD34) and platelets (CD41a) were not expressed in the stem cell populations prepared by the present invention, indicating that the obtained cells are a pure stem cell population.

In one aspect, the present invention provides a method for preparing equine amniotic fluid-derived multipotent stem cells showing the following characteristics and being more homogeneous than those before culture, comprising Step 1 of culturing stem cells isolated from equine amniotic fluid in EGM™-2 (Endothelial Cell Growth Medium-2)(Lonza, Switzerland); and Step 2 of recovering the cultured cells:

(a) showing all negative immunological characteristics with respect to the human markers CD19, CD20, CD28, CD31, CD34, CD38, CD41a, CD62L, CD62P and CD200, and showing all positive immunological characteristics with respect to the human markers CD44, CD90 and CD105;

(b) having the ability to differentiate into ectoderm, mesoderm or endoderm-derived cells; and (c) having the ability to maintain an undifferentiated state for 14 passages or more.

In a second aspect, the present invention provides a method for preparing homogeneous equine amniotic fluid-derived multipotent stem cells showing the following characteristics, comprising Step 1 of preparing equine amniotic fluid; and Step 2 of isolating multipotent stem cells, which show all negative immunological characteristics with respect to the human markers CD19, CD20, CD28, CD31, CD34, CD38, CD41a, CD62L, CD62P and CD200, and show all positive immunological characteristics with respect to the human markers CD44, CD90 and CD105, from the amniotic fluid:

(a) having the ability to differentiate into ectoderm, mesoderm or endoderm-derived cells; and (b) having the ability to maintain an undifferentiated state for 14 passages or more.

Furthermore, in a third aspect, the present invention provides equine amniotic fluid-derived multipotent stem cells having the following characteristics:

(a) showing all negative immunological characteristics with respect to the human markers CD19, CD20, CD28, CD31, CD34, CD38, CD41a, CD62L, CD62P and CD200, and showing all positive immunological characteristics with respect to the human markers CD44, CD90 and CD105;

(b) having the ability to differentiate into ectoderm, mesoderm or endoderm-derived cells; and (c) having the ability to maintain an undifferentiated state for 14 passages or more.

In the present invention, centrifugation can be performed to isolate a stem cell source from equine amniotic fluid and, in particular, centrifugation is preferably performed using a density-gradient solution. Centrifugation is performed for isolating particular cells by density gradient. Equine amniotic fluid is centrifuged using a density-gradient solution to isolate a stem cell source from the middle layer, the cell layer. More preferably, centrifugation can be performed using a Ficoll-Paque density gradient solution. Most preferably, to obtain the clear buffy coat layer by a clear density gradient, equine amniotic fluid may be diluted with PBS at a ratio of 1:1 (v:v), and then centrifuged using the Ficoll-Paque density gradient solution to remove exudates and cell debris from the resulting stem cell source.

Meanwhile, the stem cell source isolated from equine amniotic fluid did not adhere and grow in DMEM medium, but in only EGM™-2 medium. The adherent cells in EGM™-2 can be further cultured in DMEM (Dulbecco's Modified Eagle's Medium) without differentiation.

The EGM™-2 medium used in the present invention can be prepared by addition of endothelial cell growth medium-2 SingleQuot to EBM (Endothelial cell Basal Medium), and preferably, Lonza's products (Switzerland) can be used. EGM™-2 is a medium that is commonly used to culture endothelial cells (e.g., HUVEC cells).

EGM™-2 medium contains various growth factors (human-basic fibroblast growth factor; h-bFGF, vascular endothelial growth factor; VEGF, long R3-insulin-like growth factor; R3-IGF, and human epidermal growth factor; h-EGF) to facilitate cell growth and, preferably, it contains FBS as much as 10~20%.

In the present invention, a culture dish to which cells attach can be used. A fibronectin-coated culture dish can be used.

DMEM medium is produced by many companies, and thus can be easily purchased. It is possible to replace it with a cell culture medium commonly used in the art. That is, it may be MEM, alpha-MEM, DMEM, or basal medium, and preferably contains nutrients such as FBS (fetal bovine serum). Further, the DMEM medium is preferably a low-glucose DMEM.

In one preferred embodiment of the present invention, equine amniotic fluid was diluted with PBS at a ratio of 1:1 (v:v) and then centrifuged using a Ficoll-Paque density gradient solution. The isolated stem cell source was primarily cultured in an endothelial cell basal medium containing 20% FBS (fetal bovine serum) and endothelial cell growth medium-2 EGM™-2 Single Quot; Lonza, Switzerland), and the medium was then changed to 10% FBS-DMEM medium (low glucose-DMEM) and the non-attached cells were removed to obtain pure multipotent stem cells.

Meanwhile, the isolation of adult stem cells having certain cell-surface antigenic and immunological properties, for example, the isolation by treatment with antibodies can be performed using the means to detect fluorescence, magnets and nanoparticles.

The means to detect fluorescence, magnets and nanoparticles are attached to antibodies, which can be isolated by the methods utilizing immunological properties of cells including, but not limited to, Fluorescence Activated Cell Sorter (FACS) or MACS (Magnetic Activated Cell Sorter), in which the methods can be readily selected by a person of ordinary skill in the art.

Immunological characteristics of the stem cells isolated from equine amniotic fluid according to the present invention were investigated by a flow cytometric method using FACS.

In this regard, the obtained stem cell broth is collected, from which cells are isolated by, for example, centrifugation, and stained directly with antibodies; and the cells are cultured and grown in a suitable medium and then stained with antibodies.

The staining of cells is performed by mixing a primary antibody recognizing a surface antigen with a target cell sample and incubating the mixture on ice for 30 minutes to 1 hour. When the primary antibody is fluorescently labeled, the cells are isolated after washing. When the primary antibody is not fluorescently labeled, cells reacted with the primary antibody and a fluorescent labeled secondary antibody having binding activity to the primary antibody are mixed after washing, and incubated on ice for 30 minutes to 1 hour. After washing, the cells stained with the primary and secondary antibodies can be isolated.

According to one embodiment of the present invention, the equine amniotic fluid-derived multipotent stem cells prepared by the method of the present invention showed a gradual increase in CPDL up to passage 12, suggesting that these cells had a high proliferation rate. In addition, the multipotent stem cells showed continuous and steady proliferation after passage 12, and cells at passage 14 still grew, indicating that the cells have a higher self-renewal capacity than the conventional equine adipose-derived multipotent stem cells cultured for approximately 10 passages.

Therefore, the equine amniotic fluid-derived multipotent stem cells isolated according to the present invention are characterized by maintaining an undifferentiated state for 14 passages or more.

In the present invention, the equine may be any one selected from the group consisting of Subgenus *Hippotigris*, Subgenus *Equus*, mule and Subgenus *Asinus*.

In a fourth aspect, the present invention provides a method for differentiating multipotent stem cells into chondrocytes, characterized by culturing the multipotent stem cells according to the present invention in a chondrogenic induction medium. In general, the known chondrogenic induction medium consists of 10 ng/ml of TGF-beta 1, 50 uM of L-ascrobate-2-phosphate, and 6.25 ug/ml of insulin.

In a fifth aspect, the present invention provides a method for differentiating multipotent stem cells into osteocytes, characterized by culturing the multipotent stem cells according to the present invention in a culture medium containing dexamethasone, beta-glycerophosphate and ascorbic acid 2-phosphate.

In a sixth aspect, the present invention provides a method for differentiating multipotent stem cells into adipocytes, characterized by culturing the multipotent stem cells according to the present invention in a culture medium containing dexamethasone, indomethacin, 3-isobutyl methylxanthine and insulin.

According to one embodiment of the present invention, when the equine amniotic fluid-derived multipotent stem cells are cultured in a proper induction medium, they can differentiate into the mesoderm-derived cells, chondrocytes, osteocytes or adipocytes with high efficiency. Therefore, it is apparent to those skilled in the art that when appropriate stimulation is given, the cells can differentiate into the mesoderm-derived cells, tenocytes or myocytes with high efficiency. Meanwhile, it is apparent to those skilled in the art that the multipotent stem cells of the present invention exhibit the characteristics of stem cells in view of surface antigen, self-renewal ability, and morphology, and thus they can differentiate into ectoderm or endoderm-derived cells by appropriate stimulation.

Further, in one embodiment of the present invention, when the multipotent stem cells were cultured in DMEM containing 10% FBS, 0.1 µM dexamethasone, 10 mM beta-glycerophosphate, 50 µM ascorbic acid 2-phosphate to induce osteogenic differentiation, osteogenic differentiated cells showed 13-fold greater values than a control group cultured in a general culture medium, indicating excellent differentiation capability.

In a seventh aspect, the present invention provides a cell therapeutic agent comprising the multipotent stem cells according to the present invention or cells differentiated therefrom as an active ingredient.

The multipotent stem cells according to the present invention that can differentiate into chondrocytes, or chondrocytes differentiated therefrom can be used as an active ingredient in a cell therapeutic agent for the treatment of equine osteoarthritis.

The multipotent stem cells according to the present invention that can differentiate into osteocytes, or osteocytes differentiated therefrom can be used as an active ingredient in a cell therapeutic agent for the treatment of equine bone loss disease. It is apparent to those skilled in the art that the multipotent stem cells can be also used in combination with a cell therapeutic agent for equine bone injury.

The multipotent stem cells according to the present invention that can differentiate into adipocytes, or adipocytes differentiated therefrom can be used as an active ingredient in a cell therapeutic agent for the formation of equine adipose tissue.

The multipotent stem cells according to the present invention that can differentiate into tenocytes, or tenocytes differentiated therefrom can be used as an active ingredient in a cell therapeutic agent for the formation of equine tendon tissue.

The multipotent stem cells according to the present invention that can differentiate into myocytes, or myocytes differentiated therefrom can be used as an active ingredient in a cell therapeutic agent for the formation of equine muscle tissue.

As described above, since the multipotent stem cells according to the present invention are excellent in the ability to differentiate into mesoderm-derived cells such as osteocyte, chondrocyte, adipocyte, tenocyte, and myocyte, it is apparent to those skilled in the art that the cell therapeutic agents including the multipotent stem cells according to the present invention or cells differentiated therefrom as an active ingredient show excellent efficacy. Further, since the multipotent stem cells according to the present invention or cells differentiated therefrom are derived from equine amniotic fluid, it is apparent that they show lower rejection, and thus they can be particularly used in the cell therapeutic agents for equine diseases.

Hereinafter, the present invention will be described in more detail with reference to Examples. However, these Examples are for illustrative purposes only, and the invention is not intended to be limited by these Examples.

EXAMPLE 1

Acquisition of eAF-MSCs (Equine Amniotic Fluid-derived Multipotent Stem Cells)

1-1: Collection of Equine Amniotic Fluid

Equine amniotic fluid was obtained from thoroughbred mares during the foaling period in stalls at a private horse farm in South Korea. Mares when giving birth are very sensitive and the amniotic membrane can be easily ruptured by a mare. Therefore, to prevent stimulating the mare, amniotic fluid was carefully taken. The amniotic fluid samples were collected with a 30-mL syringe on an 18-gauge needle before rupturing the membrane. To prevent possible contamination, syringes and gloves were used, and all procedures were quickly performed. The samples were moved to the laboratory within 12 hours at 4° C. On average, approximately 30 mL of amniotic fluid were obtained.

1-2: Isolation of Mononuclear Cells

Isolation of MSCs from mononuclear cells has been known in the previous studies (Colter D C et al., Proc. Natl. Acad. Sci. USA. 97(7):3213-8, 2000), and mononuclear cells (MNCs) were isolated as follows. First, to obtain the clear buffy coat layer, equine amniotic fluid was diluted with PBS (Phosphate Buffered Saline) at a ratio of 1:1 (v:v). The diluted sample was centrifuged using a Ficoll-Paque density-gradient (GE healthcare, US) at 2500 rpm for 20 minutes. Mononuclear cells were harvested, and then washed with PBS several times to remove platelets and red blood cells, and finally mononuclear cells were isolated.

1-3: Culture of Mononuclear Cells and Isolation of MSCs

The mononuclear cells according to Example 1-2 were seeded on fibronectin-coated 100-mm culture dishes (Nunc, US), and incubated at 5% $CO_2$ and 37° C. The fibronectin-coated dish enhanced cell adhesion, and the culture medium consisted of Endothelial cell Basal Medium (EBM, Lonza, Switzerland) containing 20% FBS (fetal bovine serum, Gibco-BRL, US) and Endothelial cell Growth Medium-2 SingleQuot EGM™-2 Single Quot; Lonza, Switzerland). Various growth factors (human-basic fibroblast growth factor; h-bFGF, vascular endothelial growth factor; VEGF, long R3-insulin-like growth factor; R3-IGF, and human epidermal growth factor; h-EGF) in the basal medium increased initial cell growth.

After 7 days, the medium was changed to 10% FBS growth medium (low-glucose Dulbecco's Modified Eagle's Medium; low glucose-DMEM, Gibco-BRL, US) and the non-attached cells and debris were removed to obtain MSCs. Only the attached cells remained in the dish, and the morphology of the cells was observed. The growth medium was changed twice weekly until the attached cells reached 70-80% confluence.

Figure 1:
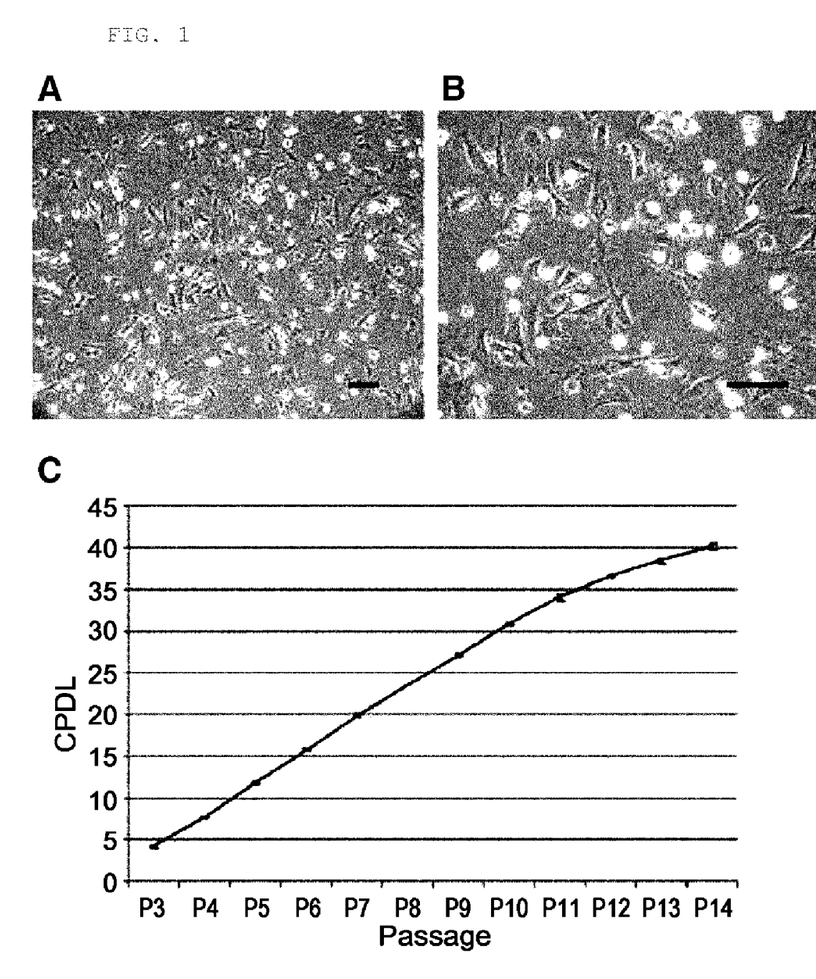
FIG. 1 shows images (1A, 1B) and a growth curve of isolated eAF-MSCs (1C)

As a result, the morphology of the cells was spindle shaped as shown in FIGS. 1A and B, showing a similar morphology as BM-MSCs (Bone marrow-Mesenchymal stem cells) or UCB-MSCs (Umbilical cord blood-Mesenchymal stem cells). Consequently, eAF-MSCs were obtained.

EXAMPLE 2

Test of Self-renewal Capacity of eAF-MSCs by Analysis of Passage Number

Stem cells, in addition to multipotent stem cells (MSCs), have self-renewal capacity. In many cases, the self-renewal ability is associated with a continuous and steady proliferation rate similar to embryonic stem cells (ESCs), hematopoietic stem cells (HSCs) and cancer stem cells (CSCs) (Reya T. et al., Nature, November 1; 414(6859):105-11, 2001). Therefore, the growth efficiency and proliferation potential of eAF-MSC were determined by the CPDL (cumulative population doubling level) of the stem cells obtained by Example 1-3.

CPDL indicates the proliferation rate of cells, and is represented by the following Formula:

$$CPDL = \ln(Nf/Ni)/\ln 2$$

(Ni: the initial seeding cell number; Nf: final harvest cell number)

The cells obtained in Example 1-3 were plated at a density of $5 \times 10^4$ in a 6-well culture plate (Nunc) and subcultured 5-7 days later. The final cell numbers were counted and $5 \times 10^4$ cells were replated. To yield CPDL, the population doubling for each passage was calculated and then added to the population doubling levels of the previous passages. The cells were passaged until a decrease in the proliferation rate was observed.

As shown in FIG. 1C, the CPDL curves showed that eAF-MSC grew until passage 14. From passage 12, the CPDL began to decrease. While the proliferation level at passage 14 was lower than that of earlier passage cells, passage 14 cells still grew. Moreover, there was no decrease in CPDL until passage 12. This result indicated that eAF-MSC had self-renewal capacity.

EXAMPLE 3

Immunophenotypic Characterization of eAF-MSCs by Flow Cytometry

In general, human MSCs show distinct cell-surface antigen markers. According to the International Society of Cellular Therapy, human MSCs show positive expression for the human markers CD73, CD44, CD90 and CD105, and negative expression for the human markers CD11b, CD14, CD18, CD79a, CD34, CD45 and HLA-DR (Dominici M. et al., Cytoherapy, 8(4):315-7, 2006). Therefore, immunophenotypic characterization of eAF-MSCs by flow cytometry was conducted as follows.

Flow cytometry analysis of eAF-MSC at passage 5, which was obtained in Example 1-3, was conducted using the human markers, 13 CD markers (CD19, CD20, CD28, CD31, CD34, CD38, CD41a, CD62L, CD62P, CD200, CD44, CD90 and CD105), as there are no various equine specific antibodies for flow cytometry.

Cells were stained in accordance with the protocol provided by BD biosciences (US). In brief, eAF-MSCs were washed twice with PBS and harvested using 0.25% trypsin/EDTA. Cells were divided into groups. Each divided aliquot contained approximately $1 \times 10^5$ cells. Mouse anti-human CD19, mouse anti-human CD20, mouse anti-human CD28, mouse anti-human CD31, mouse anti-human CD34, mouse anti-human CD38, mouse anti-human CD41a, mouse anti-human CD 44, mouse anti-human CD62L, mouse anti-human CD62P, mouse anti-human CD200, and mouse anti-human CD90 were products of BD Biosciences, and mouse anti-human CD105 was a product of Serotec (US). They were used for cell-surface antigen detection, and all antibodies were conjugated with FITC (Fluorescein isothiocyanate) or PE (phycoerythrin).

Cells were stained for 30 minutes at 4° C. After conjugating with antibody, cells were washed with PBS and resuspended in 500 μl of PBS. Analysis was carried out with a FACS Calibur™ (BD Biosciences) and Cell Quest Pro™ (BD Biosciences) software.

Figure 2:
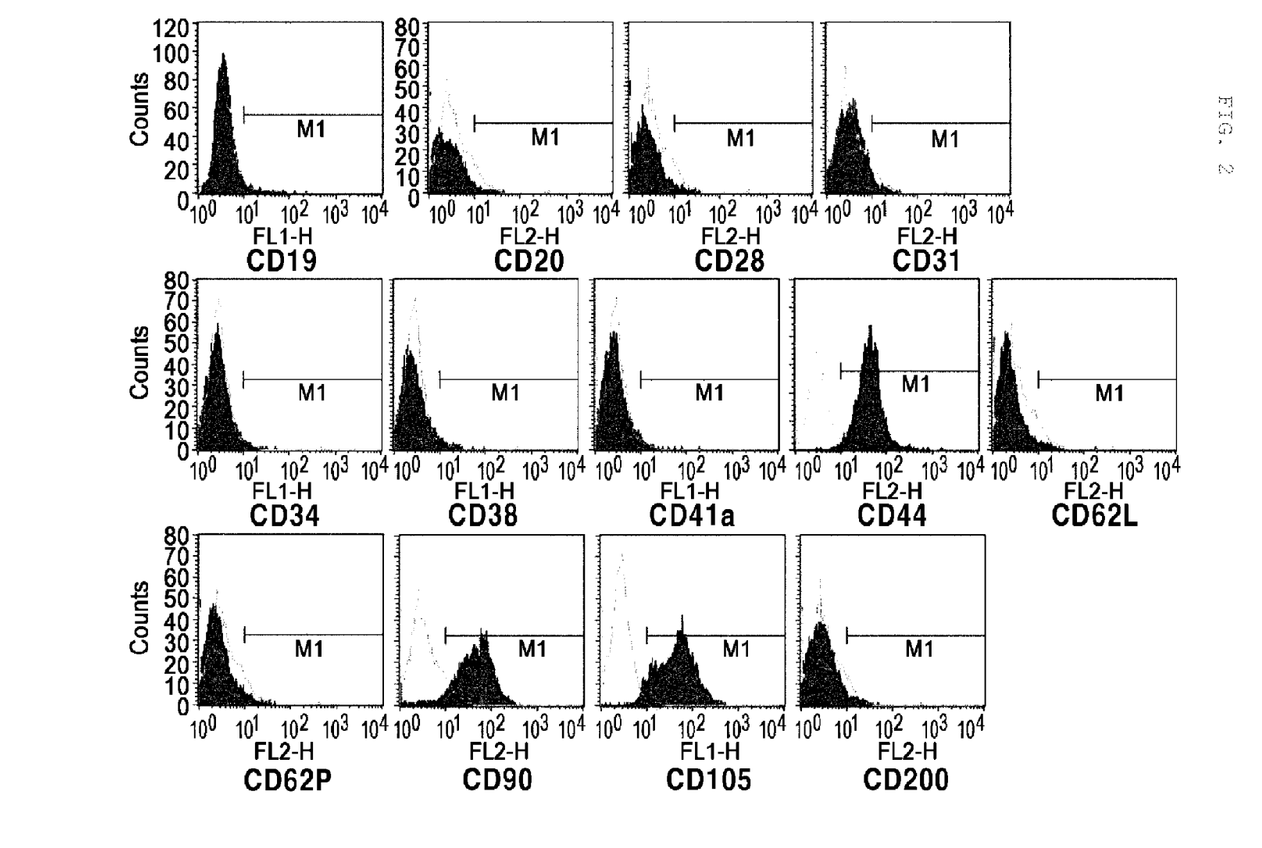
FIG. 2 shows the results of flow cytometric analysis (FACs) of eAF-MSCs.

As shown in FIG. 2 and Table 1, a similar expression pattern of MSC phenotype was observed. CD44, CD90 and CD105 snowed a positive expression pattern, indicating that eAF-MSCs are stem cells.

In contrast, the markers for immune cells CD19, CD20, CD28, CD38, CD62L, CD200, the markers for endothelial cells CD31 and CD62P, the marker for hematopoietic cells CD34 and the marker for platelets CD41a were not expressed. This result showed that eAF-MSC is a pure stem cell population having an immunophenotypic property of typical MSC.

TABLE 1

| Flow cytometric analysis of eAF-MSCs | |
|---|---|
| Marker | Percentage (%) |
| CD19 | 2.81 |
| CD20 | 1.45 |
| CD28 | 1.52 |
| CD31 | 2.38 |
| CD34 | 1.47 |
| CD38 | 1.99 |
| CD41a | 1.66 |
| CD44 | 99.47 |
| CD62L | 1.33 |

TABLE 1-continued

Flow cytometric analysis of eAF-MSCs

| Marker | Percentage (%) |
|---|---|
| CD62P | 1.87 |
| CD90 | 96.22 |
| CD105 | 95.10 |
| CD200 | 2.53 |

EXAMPLE 4

Identification of Trilineage Differentiation Capability of eAF-MSCs

To characterize the eAF-MSC, trilineage differentiation assays were performed. In general, MSCs can differentiate into chondrocytes, osteocytes and adipocytes in vitro. Therefore, to investigate differentiation of eAF-MSCs, cells were cultured in the medium suitable for each lineage.

4-1: Chondrogenic Differentiation

To investigate chondrogenic capability, eAF-MSCs obtained by the method of Example 1-3 were seeded into a 15-mL polypropylene tube and centrifuged to a pellet. The pellet was white in color and transparent in structure. The pellet was cultured at 37° C. in a 5% $CO_2$ incubator in 1 mL of chondrogenic induction medium (Lonza, Wakersville, Md., USA) (Experimental group), which was changed every 3 days for 3 weeks. Instead of the chondrogenic induction medium, cells were cultured in a growth medium under the same conditions as the control.

To confirm the inner structure of the pellet as the experimental group, the pellet was cut into 3-μm sections, and the slice on a slide was deparaffinized and hydrated with distilled water. The slide was immersed in toluidine blue (tolonium chloride), which has usually been used to confirm the morphology of cartilage tissue, for 1 minute for staining. Excessive stain was removed with several washes of distilled water. The slide was quickly dehydrated and cleared in xylene and covered with Canada balsam and a coverslip.

Figure 3:
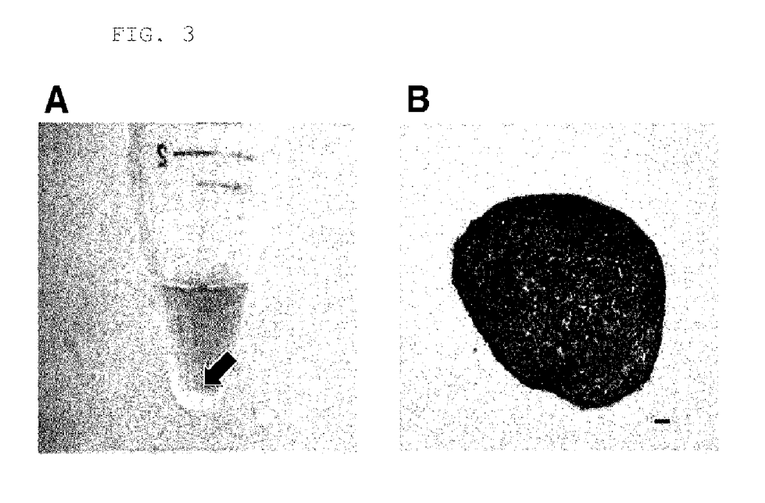
FIGS. 3A and 3B show pictures (FIG. 3A) and Toluidine blue staining of chondrogenic pellets of eAF-MSCs (FIG. 3B)

As shown in FIG. 3A, the pellet as the experimental group aggregated and formed a round-shaped structure at the bottom of the tube over time. However, it was found that the control pellets did not aggregate and all the cells entered suspension when the medium was changed, indicating that chondrogenic differentiation was not induced in the control pellet.

As shown in FIG. 3B, it was found that the pellet as the experimental group was positive for toluidine blue staining and that the morphology of the pellet approximated that of general chondrogenic tissues. The round-shaped pellets could not be separated by pipetting or vortexing. These results indicate that chondrogenic differentiation of the equine amniotic fluid-derived stem cells according to the present invention was successfully induced.

4-2: Osteogenic Differentiation

To determine osteogenesis, eAF-MSCs obtained in Example 1-3 were cultured in an osteogenic induction medium. Instead of the osteogenic induction medium, cells were cultured in the growth medium under the same conditions as the control. The medium was changed every 3 days for 2 weeks.

For osteogenic differentiation, cells were plated in a 6-well plate at a density of $1\times10^5$. After the cells were cultured until 70-80% confluency, they were treated with an osteogenic induction medium (DMEM containing 10% FBS, 0.1 μM dexamethasone, 10 mM beta-glycerophosphate, 50 μM ascorbic acid 2-phosphate; Sigma-Aldrich, US). DMEM supplemented with only FBS was used as a control group.

The medium was changed twice weekly, and cultured for 2 weeks. To confirm osteogenic differentiation, Alizarin Red S staining was performed to detect calcium deposition. Cells were rinsed with PBS and fixed with 70% ice-cold ethanol for 1 hour. After three washes using distilled water, the cells were stained using 40 mM Alizarin Red S (pH 4.2; Sigma-Aldrich) for 10 minutes at room temperature.

For quantification, the cells were rinsed with five washes of distilled water. Alizarin Red S staining was solubilized using 100 mM cetylpyridinium chloride (Sigma-Aldrich) for 1 hour. The release of the solubilized Alizarin Red S was measured at 570 nm using a spectrophotometer.

Figure 4:
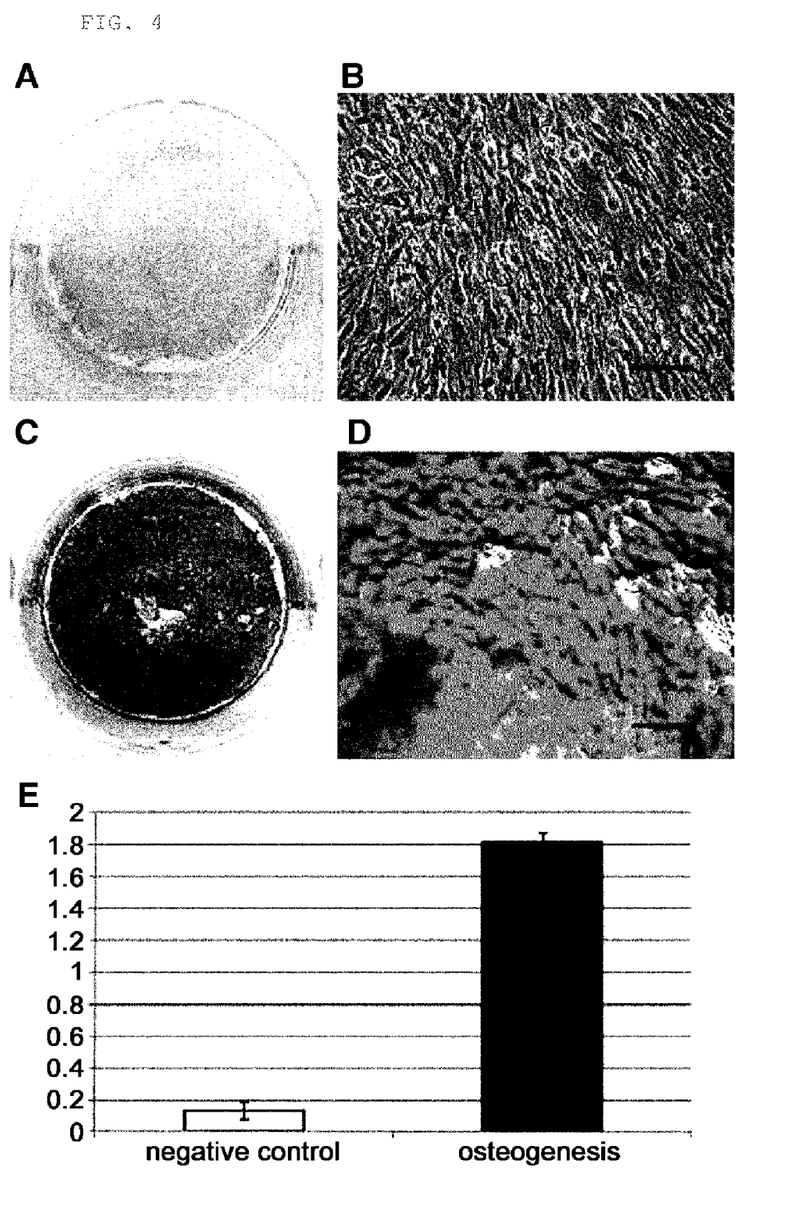
FIG. 4 shows Alizarin Red S staining of osteogenic induction of eAF-MSCs (4A, 4B: control groups; 4C, 4D: experimental groups) and a quantification graph for the staining results (4E)

As shown in FIGS. 4A to 4D, calcium mineralization formations were detected by Alizarin Red S staining. As shown in FIGS. 4C and 4D, the cells cultured in the osteogenic induction medium were Alizarin Red S-positive. As shown in FIGS. 4A and 4B, control cells were not stained. As shown in FIG. 4E, when the stained cells were quantified using cetylpyridinium chloride (Sigma-Aldrich), osteogenic differentiated cells showed 13-fold greater values than control cells. These results indicate that osteogenic differentiation of the equine amniotic fluid-derived stem cells according to the present invention was successfully induced.

4-3: Adipogenic Differentiation

For adipogenesis, cells were plated in a 6-well plate at a density of $1\times10^5$. After the cells were cultured until 90-100% confluency, they were cultured in an adipogenic induction medium (low glucose DMEM containing 10% FBS, 100 nM dexamethasone, 10 μg/ml insulin, 0.5 mM 3-isobutyl-1-methylxanthine, and 0.2 mM indomethacin).

The medium was changed every 3 days for 2 weeks, and fat droplets were detected by Oil Red O staining, which is a fat-soluble dye. Cells were photographed, and optical density was measured at 500 nm. In detail, cells were fixed with 10% formalin for approximately 1 hour and rinsed with 60% isopropanol prior to incubation in Oil Red O for 10 minutes.

Excessive stain was removed with five washes of water. Oil Red O stain was solubilized using 100% isopropanol for 1 hour and the released Oil Red O stain was measured at 500 nm using a spectrophotometer.

Figure 5:
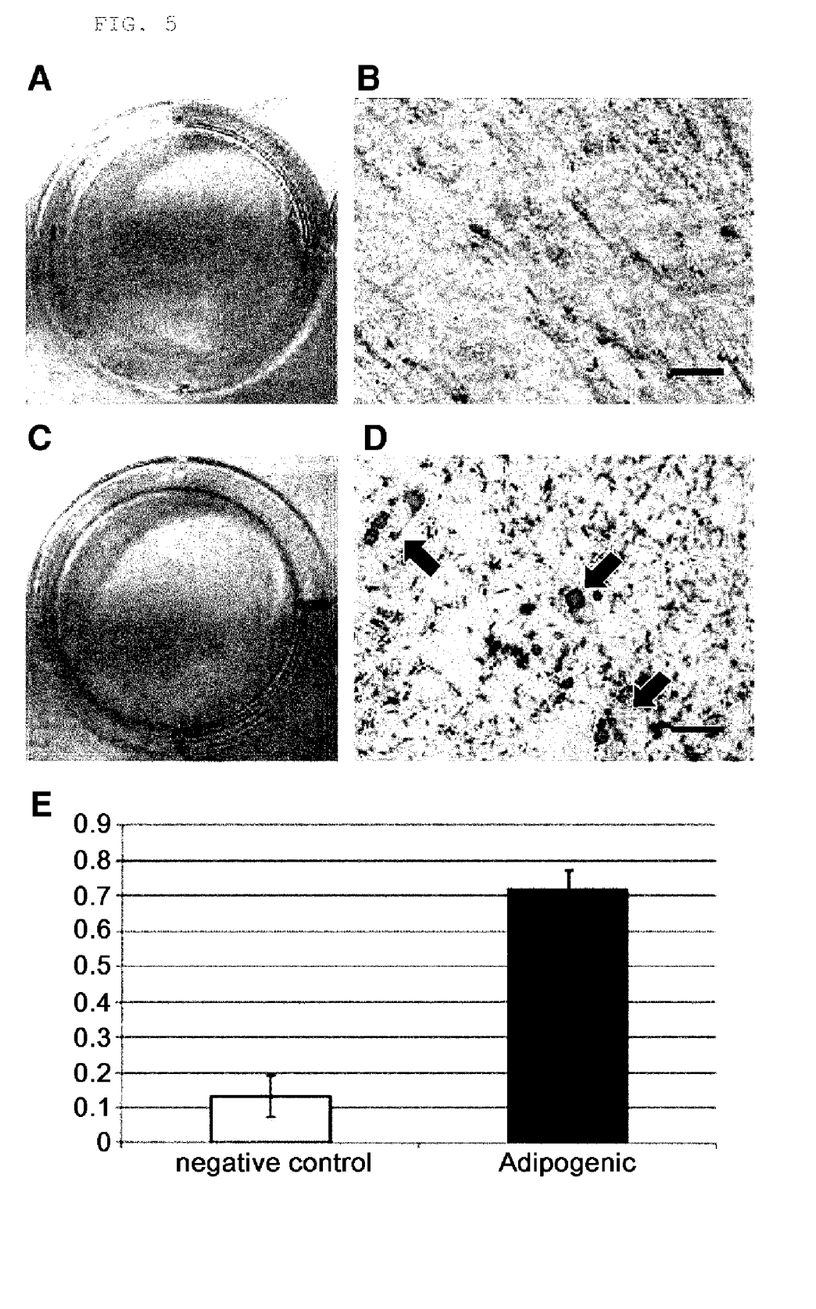
FIG. 5 shows Oil red O staining of adipogenic induction of eAF-MSCs (5A, 5B: control groups; 5C, 5D: experimental groups) and a quantification graph for the staining results (5E).

As shown in FIGS. 5A to 5D, fat droplets were not detected in the controls. In contrast, fat droplets were detected in the cells cultured in the adipogenic induction medium after 1 week. As shown in FIGS. 5C and 5D, the cells cultured in the adipogenic induction medium were Oil Red O-positive after 2 weeks, and the black arrow in FIG. 5D indicates a stained fat droplet.

As shown in FIG. 5E, when cells were quantified with isopropanol, adipogenic differentiated cells showed 5-fold greater values than control cells. These results indicate that adipogenic differentiation of the equine amniotic fluid-derived stem cells according to the present invention was successfully induced. Consequently, Example 4 confirmed that the equine amniotic fluid-derived stem cells according to the present invention are able to differentiate into mesoderm-derived cells, and they have excellent differentiation capability.

Although specific portions of the present invention were specifically described in the above, a person skilled in the art will apparently understand that such specific description is only preferable embodiments of the present invention, but the scope of the present invention is not limited by them. Accordingly, it should be understood that the practical scope of the present invention is defined only by the appended claims and equivalency thereof.

EFFECT OF THE INVENTION

The present invention confirmed that equine amniotic fluid can be a source of equine adult multipotent stem cell supply, and the equine amniotic fluid-derived multipotent stem cells prepared according to the present invention exhibit excellent self-renewal ability and differentiation capability. Therefore, the cells can be used as an active ingredient for cell therapy of horses, which requires a large amount of cells. In particular, the stem cells of the present invention having excellent self-renewal ability and differentiation capability are useful for the treatment of bone, tendon, or muscle injuries and bone loss diseases of racehorses.

What is claimed is:

1. A method for preparing equine amniotic fluid-derived multipotent stem cells, comprising
    Step 1 of isolating mononuclear cells from equine amniotic
    Step 2 of culturing the mononuclear cells in basal culture media for a period time, wherein the cultured mononuclear cells are adherent; and
    wherein the basal culture media comprises an endothelial cell growth media containing vascular endothelial growth factor (VEGF), long $R^3$-insulin-like growth factor; ($R^3$-IGF), and human epidermal growth factor(h-EGF); and
    Step 3 of culturing the adherent cells in Dulbecco's Modified Eagle's Medium (DMEM) after culturing in the basal media; and
    Step 4 of recovering the stem cells from the culture, wherein the recovered multipotent stem cells:
    (a) are negative for the human markers CD19, CD20, CD28, CD31, CD34, CD38, CD41a, CD62L, CD62P, and CD200, and
    (b) are positive the human markers CD44, CD90, and CD105;
    (c) have the ability to differentiate into, mesoderm derived cells;
    (d) have the ability to maintain an undifferentiated state for 14 passages or more; and
    (e) are more homogeneous than those before culture.

2. The method according to claim 1, isolation of the mononuclear cells is performed with a density-gradient solution and the mononuclear cells is performed with a density-gradient solution and the mononuclear cells are isolated from a middle layer.

3. The method according to claim 1, wherein the cells are adherent and cultured in monolayer.

4. The method according to claim 1, wherein the basal culture media contains fetal bovine serum (FBS).

5. The method according to claim 1, wherein the DMEM is low glucose-DMEM containing FBS.

6. A method for differentiating multipotent stem cells into chondrocytes, comprising:
    preparing equine amniotic fluid-derived multipotent stem cells by the method of claim 1; and
    culturing the multipotent stem cells in a chondrogenic induction medium.

7. A method for differentiating multipotent stem cells into osteocytes, comprising:
    preparing equine amniotic fluid-derived multipotent stem cells by the method of claim 1; and
    culturing the multipotent stem cells in a culture medium comprising dexamethasone, beta-glycerophosphate and ascorbic acid 2-phosphate.

8. A method for differentiating multipotent stem cells into adipocytes, comprising:
    preparing equine amniotic fluid-derived multipotent stem cells by the method of claim 1; and
    culturing the multipotent stem cells in a culture medium comprising dexamethasone, indomethacin, 3-isobutyl methylxanthine and insulin to make adipocytes.

* * * * *